United States Patent
Filippatos et al.

(10) Patent No.: US 11,766,307 B2
(45) Date of Patent: Sep. 26, 2023

(54) METHOD AND DEVICE FOR CREATING AND DISPLAYING A MAP OF A BRAIN OPERATING FIELD

(71) Applicant: Carl Zeiss Meditec AG, Jena (DE)

(72) Inventors: Konstantinos Filippatos, Munich (DE); Roland Guckler, Ulm (DE); Annette Schreiber, Aying (DE)

(73) Assignee: Carl Zeiss Meditec AG, Jena (DE)

( * ) Notice: Subject to any disclaimer, the term of this patent is extended or adjusted under 35 U.S.C. 154(b) by 307 days.

(21) Appl. No.: 17/025,936

(22) Filed: Sep. 18, 2020

(65) Prior Publication Data
US 2021/0085423 A1    Mar. 25, 2021

(30) Foreign Application Priority Data
Sep. 20, 2019  (DE) .................. 10 2019 125 413.2

(51) Int. Cl.
*A61B 90/20* (2016.01)
*A61B 5/00* (2006.01)

(52) U.S. Cl.
CPC ............. *A61B 90/20* (2016.02); *A61B 5/743* (2013.01); *A61B 5/7425* (2013.01)

(58) Field of Classification Search
CPC ....... A61B 90/20; A61B 5/7425; A61B 5/743; A61B 5/4064
USPC ....................................................... 600/476
See application file for complete search history.

(56) References Cited

U.S. PATENT DOCUMENTS

| | | | |
|---|---|---|---|
| 5,215,095 A | 6/1993 | Macvicar et al. | |
| 7,953,261 B2 * | 5/2011 | Nishimura | G06V 20/69 382/128 |
| 8,413,079 B2 * | 4/2013 | Oda | A61B 1/041 382/128 |

(Continued)

FOREIGN PATENT DOCUMENTS

| | | | |
|---|---|---|---|
| DE | 10 2008 040 807 A1 | 2/2010 | |
| EP | 2 542 141 B1 | 4/2016 | |
| WO | WO-2016149416 A1 * | 9/2016 | ........... A61B 3/0008 |

OTHER PUBLICATIONS

Oelschlaegel, M. et al, "Intraoperative identification of somatosensory brain areas using optical imaging and standard RGB camera equipment—a feasibility study", Current Directions in Biomedical Engineering 2015, 1:265-269.

(Continued)

*Primary Examiner* — John Denny Li
(74) *Attorney, Agent, or Firm* — Walter Ottesen, P.A.

(57) ABSTRACT

A method and device are for generating and displaying a map of a brain operating field, brain tissue areas associated with a stimulated brain function being marked in the map. In the method, during a measurement cycle a stimulation of a brain function is effected and a stimulation image of the brain operating field with the stimulated brain function is recorded, a reference image without the stimulated brain function is recorded, the stimulation image and the reference image are used to generate the map, and the map is displayed on a display. A plurality of cycles are performed. A new map is generated after each cycle following the first cycle. In order to generate the new map, the stimulation and reference images of one or more preceding cycles are used besides the images recorded in the cycle just carried out. At least the new map is displayed after each cycle.

28 Claims, 5 Drawing Sheets

(56) References Cited

U.S. PATENT DOCUMENTS

| | | | |
|---|---|---|---|
| 9,025,847 B2 | 5/2015 | Kitamura et al. | |
| 9,095,255 B2 | 8/2015 | Fanenbruck | |
| 9,801,549 B2 | 10/2017 | Panitz et al. | |
| 2002/0099295 A1* | 7/2002 | Gil | A61B 5/4064 600/323 |
| 2002/0188174 A1* | 12/2002 | Aizawa | A61B 5/064 600/109 |
| 2009/0234236 A1 | 9/2009 | Lomnes et al. | |
| 2010/0042000 A1 | 2/2010 | Schuhrke et al. | |
| 2014/0067279 A1* | 3/2014 | George | A61B 5/7278 702/19 |
| 2015/0272468 A1* | 10/2015 | Liu | A61B 5/0042 600/410 |
| 2017/0071471 A1* | 3/2017 | Yamagata | A61B 5/4029 |
| 2017/0303844 A1 | 10/2017 | Baker et al. | |
| 2019/0151043 A1* | 5/2019 | Wada | G06T 15/08 |
| 2019/0324252 A1* | 10/2019 | Mak | G02B 21/06 |
| 2022/0265121 A1* | 8/2022 | Fouts | A61B 1/00006 |

OTHER PUBLICATIONS

Sato, K. et al., "Intraoperative intrinsic optical imaging of human somatosensory cortex during neurosurgical operations", Neurophotonics, SPIE Digital Library, Jul.—Sep. 2017, vol. 4(3), 031205, pp. 1 to 5.

Sobottka, S. et al, "Intraoperative optical imaging of intrinsic signals: a reliable method for visualizing stimulated functional brain areas during surgery", J. Neurosurg. Oct. 2013, 119:853-863.

* cited by examiner

METHOD AND DEVICE FOR CREATING AND DISPLAYING A MAP OF A BRAIN OPERATING FIELD

CROSS REFERENCE TO RELATED APPLICATION

This application claims priority of German patent application no. 10 2019 125 413.2, filed Sep. 20, 2019, the entire content of which is incorporated herein by reference.

FIELD OF THE INVENTION

The present disclosure relates to a method and a device for creating and displaying a map of a brain operating field. In addition, the disclosure relates to a computer program and a data processing system for creating and displaying a map of a brain operating field, and to a nontransitory computer-readable storage medium.

BACKGROUND OF THE INVENTION

When resecting brain tumors, the surgeon is presented with the challenge of removing the tumor as completely as possible and of damaging as little healthy tissue as possible in the process. In particular, brain areas of particular importance ought to be conserved, for example the visual cortex, which is responsible for vision, or the sensory cortex, which is responsible for the sense of touch.

Methods such as functional magnetic resonance imaging, for example, allow the relative position of the tumor and of functional brain tissue areas to be determined preoperatively. This makes it possible to determine preoperatively the brain tissue areas to be conserved, and to prepare a resection of the brain tumor that is as conserving as possible. However, the brain tissue may shift when the skull is opened up (trepanation)—this is referred to as brain shift—and for this reason it is necessary to verify the relative position of the functional brain tissue areas within the exposed brain tissue. Such a verification can be effected via intraoperative mapping of the functional brain tissue areas (so-called brain mapping). By way of example, mapping can be effected here on the basis of measuring electrical signals on the surface of the brain tissue, the signals being triggered by peripheral stimulation at the extremities, for example.

An existing contactless alternative to mapping via electrical signals is so-called intraoperative optical imaging (IOI), which involves determining the change in the perfusion or the change in the oxygen content in the blood upon a changeover between stimulation and non-stimulation of certain brain functions. In this case, the perfusion and/or the oxygen content of the blood can be measured by way of a change in the spectral properties of the reflection image of the brain tissue in the region of the trepanation. By way of example, methods for interoperative optical imaging are described in M. Oelschlagel et al. "Intraoperative identification of somato-sensory brain areas using optical imaging and standard RGB camera equipment—a feasibility study", Current Directions in Biomedical Engineering 2015; 1: 265-269, in K. Sato "intraoperative intrinsic optical imaging of human somatosensory cortex during neurosurgical operations" in Neurophotonix 4 (3), 031205 (July to September 2017) and in S. B. Sobottka "Intraoperative optical imaging of intrinsic signals: a reliable method for visualizing stimulated functional brain areas during surgery" in J. Neurosurg. 119 (2013), pages 853 to 863.

Devices for intraoperative optical imaging are also integrated in surgical microscopes. By way of example, such surgical microscopes are described in US 2010/0042000 A1, U.S. Pat. Nos. 5,215,095 A1, 9,095,255 B2, 9,801,549 B2 and US 2009/0234236 A1. In this case, use is made of the fact that surgical microscopes generally have a camera for documenting the progress of surgery anyway, which camera can also be used for recording the signal for intraoperative optical imaging. A so-called activity map, that is, a map of the exposed brain tissue which indicates brain tissue areas associated with a stimulated brain function, is then created on the basis of the data obtained by intraoperative optical imaging.

For the purposes of creating the map, images of the brain operating field are recorded during a recording time period, wherein phases in which a specific brain function is stimulated alternate with phases without stimulation during the recording time period. In the method described in M. Oelschlagel et al., the intraoperative optical imaging is effected for example over a time period of 9 minutes, wherein 30-second stimulation phases alternate with 30-second rest phases, that is, phases without stimulation. The measurement signal finally used to create the map results here from the different perfusion of the brain tissue area during the stimulation and during the rest phases and/or from the different oxygen content of the blood during the stimulation phases and the rest phases.

By comparison with mapping via electrical signals, wherein electrodes are applied to the surface of the brain tissue, intraoperative optical imaging affords the advantage of not needing to touch the brain tissue during the measurement. On the other hand, however, it is not simple to detect a change in the perfusion or a change in the oxygen content of the blood via optical measurement (and without fluorescence) since the signals to be recorded are weak. For this reason, the measurement with the aid of intraoperative imaging is effected over a relatively long period of time, for example over the aforementioned 9 minutes with alternating 30-second stimulation phases and 30-second rest phases.

The treating surgeon is under great time pressure during brain surgery since the intervention that is critical for the patient is intended to be carried out as quickly as possible. At the same time, the surgeon has to accomplish highly complex procedures. Against this background, endeavors are made to assist the surgeon as well as possible during the operation.

SUMMARY OF THE INVENTION

It is therefore an object of the invention to provide a method and a device for assisting a surgeon during a brain operation, wherein the method and the device, respectively, create a map of a brain operating field which displays brain tissue areas associated with at least one stimulated brain function.

Further objects of the invention include providing a computer program, a processing system and a nontransitory computer-readable storage medium which can be used to assist a surgeon during a brain operation. The objects can, for example, also be achieved via a method for assisting a surgeon during a brain operation as disclosed herein, a computer-implemented method for assisting a surgeon during a brain operation as disclosed herein, a device for assisting a surgeon during a brain operation as disclosed herein, a computer program as disclosed herein, a data processing system as disclosed herein and a nontransitory computer-readable storage medium as disclosed herein.

In the method for creating or generating a map of a brain operating field, brain tissue areas associated with at least one stimulated brain function being marked in the map, during a measurement cycle a stimulation of at least one brain function is effected, wherein at least one stimulation image of the brain operating field with the stimulated brain function is recorded, that is, an image containing an optical signal caused by the stimulation. In this case, the optical signal may be based, for example, on an increased perfusion caused by the stimulation and/or on an increased oxygen content in the blood caused by the stimulation. In addition, during the measurement cycle at least one reference image of the brain operating field without the stimulated brain function is recorded. The at least one stimulation image recorded in the measurement cycle and the at least one reference image recorded in the measurement cycle are then used to create the map of the brain operating field, the map then being displayed on a display device, for instance a monitor. The map then represents for example those brain tissue areas which have an increased blood flow and/or an increased oxygen content of the blood during the stimulation.

According to the disclosure, a plurality of measurement cycles are carried out, and a new map of the brain operating field is created after each measurement cycle following the first measurement cycle. In order to create the new map of the brain operating field, the stimulation images and reference images of one or more preceding measurement cycles are also used besides the at least one stimulation image recorded in the measurement cycle just carried out and the at least one reference image recorded in the measurement cycle just carried out. At least the new map created after the measurement cycle just carried out is displayed after each measurement cycle. Preferably, moreover, after each measurement cycle following the first measurement cycle, in each case at least that map which was created before the new map created after the measurement cycle just carried out is also displayed.

By virtue of the fact that a new map is created after each measurement cycle following the first measurement cycle, substantially all previously recorded stimulation images and reference images being used for creating the new map, there is an improvement in the quality of the maps, in particular the signal-to-noise ratio of the maps, after each measurement cycle. The surgeon thereby has the possibility of assessing the quality of the measurement and of the map after each measurement cycle and, in the event of a sufficient quality of the map being attained, of resuming the operation at the earliest possible point in time or of continuing the operation without waiting for further measurement cycles. On the other hand, the surgeon is also enabled to estimate at an early stage whether a sufficient quality should be expected at all within a measurement time period predefined for the measurement, for example within the 9 minutes with alternating 30-second stimulation phases and 30-second rest phases as described in the introduction, since, after each process of creating a new map, it is possible to estimate whether and to what extent the quality of the map has improved vis à vis the preceding map. If it emerges at an early stage that a sufficient quality of the map should not be expected in the measurement time period, the measurement can already be terminated before the end of the measurement time period and be restarted with new parameters, for example a new orientation of the surgical microscope, an alteration of the lighting, et cetera. To estimate whether and to what extent the quality of the maps improves with each newly created map, it is advantageous if after each measurement cycle following the first measurement cycle, besides the current, newly created map, in each case at least that map which was created before the map created after the measurement cycle just carried out is also displayed. It is particularly advantageous if all previously created maps are displayed since the map quality trend is then able to be estimated particularly easily.

Typically, during a measurement cycle, a plurality of stimulation images and reference images are recorded and from each measurement cycle in each case the plurality of recorded stimulation images and reference images are used for creating the map of the brain operating field. In particular, the intraoperative optical imaging can be effected via a video camera, the frames obtained during a stimulation phase and a rest phase of a measurement cycle then being used in each case. With the first measurement cycle, only the frames of this measurement cycle are available here. As the number of measurement cycles increases, the number of frames used increases, as a result of which the quality of the map created on the basis of the frames is improved.

In order to create the map, the stimulation images and the reference images can be sorted according to their temporal sequence, which is automatically the case when a video is recorded. Then a frequency spectrum is formed from the sorted temporal sequence of the stimulation images and reference images and the map is formed from those pixels which have intensities that fluctuate with the frequency of the successive measurement cycles, for example by the corresponding pixels being marked in color in an image of the brain operating field or by contiguous regions of pixels which have intensities that fluctuate with the frequency of the successive measurement cycles being marked by a border in an image of the brain operating field. By virtue of the fact that as the number of measurement cycles increases, the number of stimulation images and reference images on which the frequency spectrum is based increases, there is an improvement in the quality of the frequency spectrum and thus the quality of the map.

In the context of the method, a maximum number of measurement cycles can be predefinable, wherein the number of the measurement cycle after which the respective map was created can then also be displayed besides the created map or the created maps. The surgeon thereby has an overview as to the current stage of the intraoperative optical imaging process and thus has an indicator of how long it will still take until the maximum number of measurement cycles is reached. Preferably, the method additionally affords a possibility of already terminating the creating of maps before reaching the maximum number of measurement cycles. This possibility can be used by the surgeon, for example, if the quality of the created map is already sufficient before the maximum number of measurement cycles is reached, or it is evident from the maps created up until then that a sufficient quality should not be expected even after the maximum number of measurement cycles. In the latter case, the surgeon can terminate the creating of maps at an early stage and start a new measurement with new parameters, for example a new orientation of the surgical microscope or new lighting parameters.

In one particularly advantageous configuration of the method, the stimulation images and reference images used for creating a map are examined for disturbances, for example for reflections, bleeding, brain shift, et cetera. The disturbances that occurred in the stimulation images and reference images on which the created map is based are then also displayed besides the created map. Additionally or alternatively, a quality parameter assigned to the created map can also be displayed besides the map, the quality parameter representing a measure of the disturbances that occurred in the stimulation images and reference images on which the created map is based. Displaying the disturbance that occurred and/or the quality parameter enables the surgeon to make a sound estimation of the quality of the map respectively created. Moreover, the display of the disturbances and/or of the quality parameter makes it possible to better estimate whether a map of sufficient quality should be expected at the end of the intraoperative optical imaging process. If it should be expected that a map with sufficient quality cannot be created, the surgeon can terminate the intraoperative optical imaging process and restart, for example with a new orientation of the surgical microscope, different lighting parameters, after stopping bleeding, et cetera.

For the case where relevant disturbances are present only in a few measurement cycles and/or the quality parameter indicates a poor quality only in a few measurement cycles, it is advantageous if, after the end of all the measurement cycles, each map created after a measurement cycle together with the disturbances that occurred in the stimulation images and reference images on which the respective map is based, and/or together with the quality parameter assigned to the respective map, are displayed and the method affords the user the possibility of sorting out individual measurement cycles and of newly creating a new map on the basis of the stimulation images and reference images of the measurement cycles that have not been sorted out. In this way, the surgeon has the possibility of basing the creation of a map only on stimulation images or reference images which can ensure a high quality of the created map.

To prepare for the intraoperative optical imaging, it can be advantageous if before the first measurement cycle, indicators are determined for parameters which are relevant to the stimulation and to the recording of the stimulation images and the reference images, and the indicators are displayed. The indicators can indicate, for example, the degree of alignment of the recording device and/or of the lighting device in relation to the brain operating field, the extent of reflections occurring, the extent of maskings, et cetera. With the aid of the indicators, before the beginning of the intraoperative optical imaging process the surgeon can then estimate whether disturbances should be expected or whether a sufficient quality of the map can be achieved with the settings effected. By way of example, in this way it is possible to avoid a situation in which the intraoperative optical imaging is effected with lighting parameter values that lead to reflections on the brain tissue, or in which intraoperative optical imaging is effected without the recording device being suitably aligned, or in which intraoperative optical imaging takes place with bleeding masking parts of the brain operating field or with some other masking.

In addition, a computer-implemented method for creating and displaying a map of a brain operating field, brain tissue areas associated with at least one stimulated brain function being marked in the map, is made available in the context of the disclosure. In the computer-implemented method, control signals are generated for controlling a stimulation device and a recording device in such a way that during a measurement cycle a stimulation of at least one brain function is effected and at least one stimulation image of the brain operating field with the stimulated brain function is recorded, and that during the measurement cycle at least one reference image of the brain operating field without the stimulated brain function is recorded. The at least one stimulation image recorded in the measurement cycle and the at least one reference image recorded in the measurement cycle are then used to create the map of the brain operating field. In addition, a signal for a display device is created and output to the display device, which signal has the effect that the map is displayed on the display device. In the computer-implemented method, the control signals for the stimulation device and the recording device are generated in such a way that a plurality of measurement cycles are carried out and a new map of the brain operating field is created after each measurement cycle following the first measurement cycle. In this case, in order to create the new map, the stimulation images and reference images of one or more preceding measurement cycles are also used besides the at least one stimulation image recorded in the measurement cycle just carried out and the at least one reference image recorded in the measurement cycle just carried out. After each measurement cycle the signal for the display device is updated in such a way that at least the new map created after the measurement cycle just carried out is displayed on the display device.

The computer-implemented method makes it possible to carry out the method for creating and displaying a map of a brain operating field using an apparatus having a camera suitable for recording stimulation images and reference images and having a display device such as a monitor or a display, for instance, a computer and a stimulation device suitable for stimulating brain functions and to realize the properties and advantages over the prior art as described with reference to the method for creating and displaying a map of a brain operating field.

The computer-implemented method can be developed in accordance with the above-described method for creating and displaying a map of a brain operating field.

The computer-implemented method can be developed in such a way that after each measurement cycle following the first measurement cycle, the signal for the display device is updated in such a way that in each case at least that map which was created before the map created after the measurement cycle just carried out is also displayed on the display device.

The computer-implemented method according to the disclosure can be developed in such a way that
  the stimulation device and the recording device are controlled in such a way that a plurality of stimulation images and reference images are recorded during a measurement cycle, and
  from each measurement cycle in each case the plurality of recorded stimulation images and reference images are used for creating the map of the brain operating field. In this case, for the purposes of creating the map, the stimulation images and the reference images can be sorted according to their temporal sequence. Then a frequency spectrum is formed from the sorted temporal sequence of the stimulation images and reference images and the map is formed from those pixels which have intensities that fluctuate with the frequency of the successive measurement cycles.

The computer-implemented method can be developed in such a way that a maximum number of measurement cycles is predefinable and the signal for the display device is created in such a way that the number of the measurement cycle after which the most up-to-date of the displayed maps was created is also displayed besides the map or the maps on the display device. In this case, there can be a possibility of terminating the creating of maps before reaching the maximum number of measurement cycles.

The computer-implemented method can be developed in such a way that the stimulation images and reference images used for creating a map are examined for disturbances. The signal for the display device is then created in such a way that the disturbances that occurred in the stimulation images and reference images on which the created map is based are also displayed besides the created map on the display device and/or a quality parameter assigned to the created map is also displayed besides the map on the display device, the quality parameter representing a measure of the disturbances that occurred in the stimulation images and reference images on which the created map is based. In particular, after the end of all the measurement cycles, each map created after a measurement cycle together with the disturbances that occurred in the stimulation images and reference images on which the respective map is based, and/or together with the quality parameter assigned to the respective map, can be displayed and the user is afforded the possibility of sorting out individual measurement cycles and of newly creating a new map on the basis of the stimulation images and reference images of the measurement cycles that have not been sorted out.

The computer-implemented method can be developed such that the stimulation device and the recording device are controlled in such a way that, before the first measurement cycle, indicators are determined for parameters which are relevant to the stimulation and to the recording of the stimulation images and the reference images, and the indicators determined are displayed.

The properties and advantages realized with the corresponding developments of the method for creating and displaying a map of a brain operating field can likewise be realized with the described developments of the computer-implemented method. Therefore, for the description of the properties and advantages of the developments of the computer-implemented method, reference is made to the above description of the developments of the method for creating and displaying a map of a brain operating field.

In addition, a device for creating and displaying a map of a brain operating field, brain tissue areas associated with at least one stimulated brain function being marked in the map, is made available in the context of the disclosure. The device includes a stimulation device, a recording device, a display device and a control and evaluation device, which is connected or connectable to the stimulation device, the recording device and the display device. The control and evaluation device is embodied in such a way that it
  controls the stimulation device and the recording device in such a way that during a measurement cycle a stimulation of at least one brain function is effected and at least one stimulation image of the brain operating field with the stimulated brain function is recorded, and that during the measurement cycle at least one reference image of the brain operating field without the stimulated brain function is recorded,
  uses the at least one stimulation image recorded in the measurement cycle and the at least one reference image recorded in the measurement cycle to create the map of the brain operating field, and
  creates a signal for a display device and outputs it to the display device, which signal has the effect that the map is displayed on the display device.

According to the disclosure, the control and evaluation device can be additionally embodied in such a way that it
  controls the stimulation device and the recording device in such a way that a plurality of measurement cycles are carried out,
  creates a new map of the brain operating field after each measurement cycle following the first measurement cycle, wherein, in order to create the new map, the stimulation images and reference images of one or more preceding measurement cycles are also used besides the at least one stimulation image recorded in the measurement cycle just carried out and the at least one reference image recorded in the measurement cycle just carried out, and
  updates the signal for the display device after each measurement cycle in such a way that at least the map created after the measurement cycle just carried out is displayed on the display device.

The device makes it possible to carry out the method for creating and displaying a map of a brain operating field and to realize the properties and advantages described with reference to the method for creating and displaying a map of a brain operating field. The recording device and/or the display device and/or the control and evaluation device can be integrated in a surgical microscope. In particular, the entire device can be part of a surgical microscope system that also includes the stimulation device besides the recording device, the display device and the control and evaluation device.

The device can be developed in such a way that it makes it possible to implement the developments of the above-described method for creating and displaying a map of a brain operating field.

The device can be developed such that after each measurement cycle following the first measurement cycle, the control and evaluation device updates the signal for the display device in such a way that in each case at least that map which was created before the map created after the measurement cycle just carried out is also displayed on the display device.

The device can be developed such that the control and evaluation device
  controls the stimulation device and the recording device in such a way that a plurality of stimulation images and reference images are recorded during a measurement cycle, and
  uses from each measurement cycle in each case the plurality of recorded stimulation images and reference images for creating the map of the brain operating field. In this case, the control and evaluation device, for creating the map,
  can sort the stimulation images and the reference images according to their temporal sequence,
  can form a frequency spectrum from the sorted temporal sequence of the stimulation images and reference images and
  can form the map from those pixels which have intensities that fluctuate with the frequency of the successive measurement cycles.

The device can be developed such that the control and evaluation device makes it possible to predefine a maximum number of measurement cycles and creates the signal for the display device in such a way that the number of the measurement cycle after which the most up-to-date of the displayed maps was created is also displayed besides the map or the maps on the display device. In this case, the control and evaluation device can afford a possibility of terminating the creating of maps before reaching the maximum number of measurement cycles.

The device can be developed such that the control and evaluation device examines the stimulation images and reference images used for creating a map for disturbances and creates the signal for the display device in such a way that the disturbances that occurred in the stimulation images and reference images on which the created map is based are also displayed besides the created map on the display device and/or a quality parameter assigned to the created map is also displayed besides the map on the display device, the quality parameter representing a measure of the disturbances that occurred in the stimulation images and reference images on which the created map is based. In this case, the control and evaluation device can create the signal for the display device in such a way that, after the end of all the measurement cycles, each map created after a measurement cycle together with the disturbances that occurred in the stimulation images and reference images on which the respective map is based, and/or together with the quality parameter assigned to the respective map, are displayed. The control and evaluation device then affords the user the possibility of sorting out individual measurement cycles and of causing a new map to be newly created on the basis of the stimulation images and reference images of the remaining measurement cycles.

The device can be developed such that the control and evaluation device controls the stimulation device and the recording device in such a way that, before the first measurement cycle, indicators are determined for parameters which are relevant to the stimulation and to the recording of the stimulation images and the reference images, and causes the indicators determined to be displayed on the display device.

The properties and advantages described with reference to the corresponding developments of the method for creating and displaying a map of a brain operating field can be realized with the described developments of the device. Therefore, with regard to the properties and advantages of the developments of the device, reference is made to the above description of the developments of the method for creating and displaying a map of a brain operating field.

In addition, a computer program for creating and displaying a map of a brain operating field, brain tissue areas associated with at least one stimulated brain function being marked in the map, is made available in the context of the disclosure. The computer program includes instructions which, when they are executed on a computer, cause the computer to carry out the steps of the computer-implemented method. In this case, the computer program can also include instructions for carrying out the steps of the developments of the computer-implemented method.

In addition, a data processing system for creating and displaying a map of a brain operating field, brain tissue areas associated with at least one stimulated brain function being marked in the map, is made available in the context of the disclosure. The data processing system comprises a processor and at least one memory. The processor is configured, on the basis of instructions of a computer program according to the disclosure, the computer program being stored in the memory, to carry out the steps of the computer-implemented method. In this case, the computer program can also include instructions for carrying out the steps of the developments of the computer-implemented method.

In addition, a nontransitory computer-readable storage medium with instructions stored thereon for creating and displaying a map of a brain operating field, brain tissue areas associated with at least one stimulated brain function being marked in the map, is made available in the context of the disclosure. When they are executed on a computer, the instructions stored on the nontransitory computer-readable storage medium cause the computer to carry out the steps of the computer-implemented method. In this case, the instructions stored on the nontransitory computer-readable storage medium can also include instructions which, when they are executed on a computer, cause the computer to carry out the steps of the developments of the computer-implemented method.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
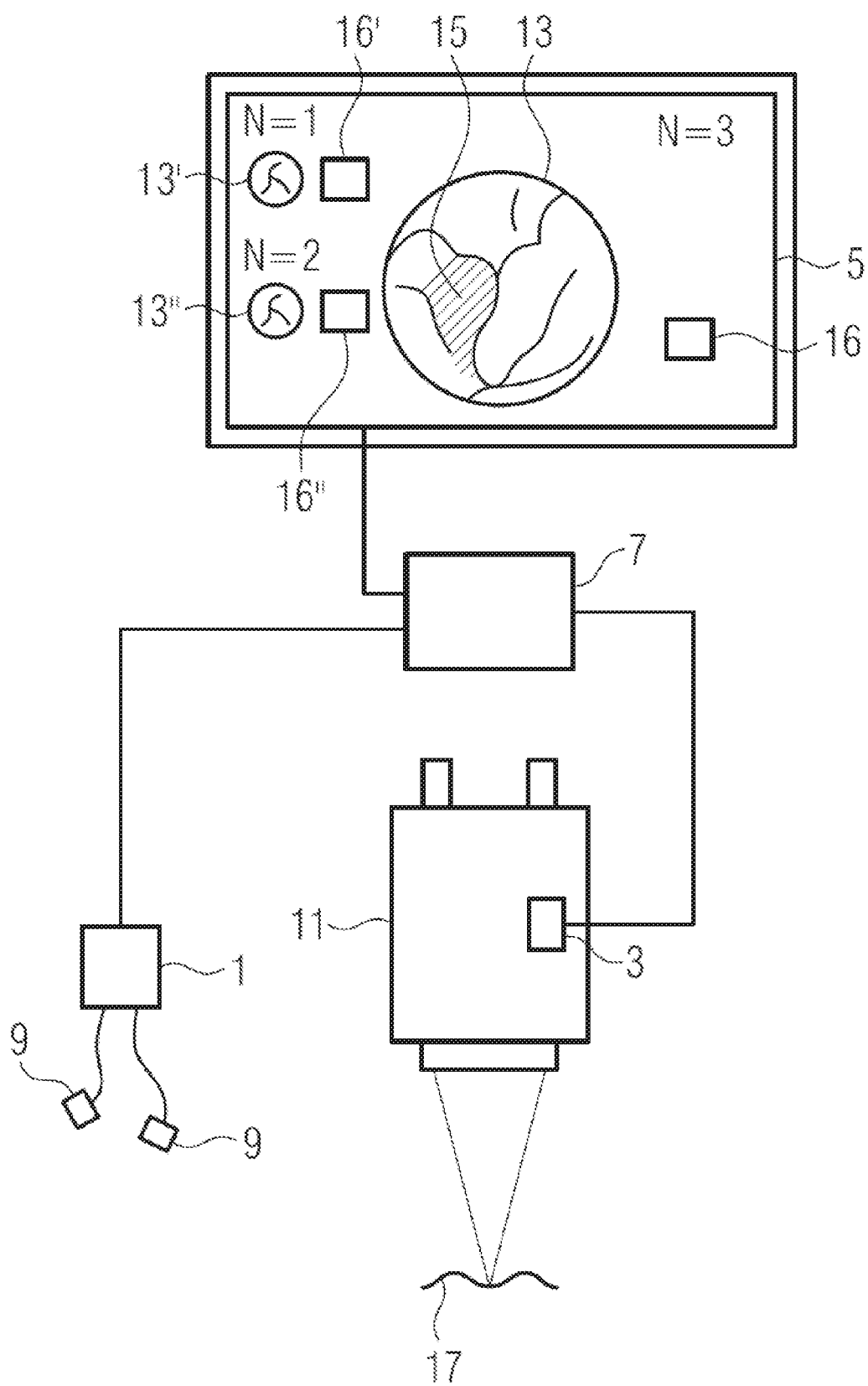
FIG. 1 shows a device for creating and displaying a map of a brain operating field.
Figure 2:
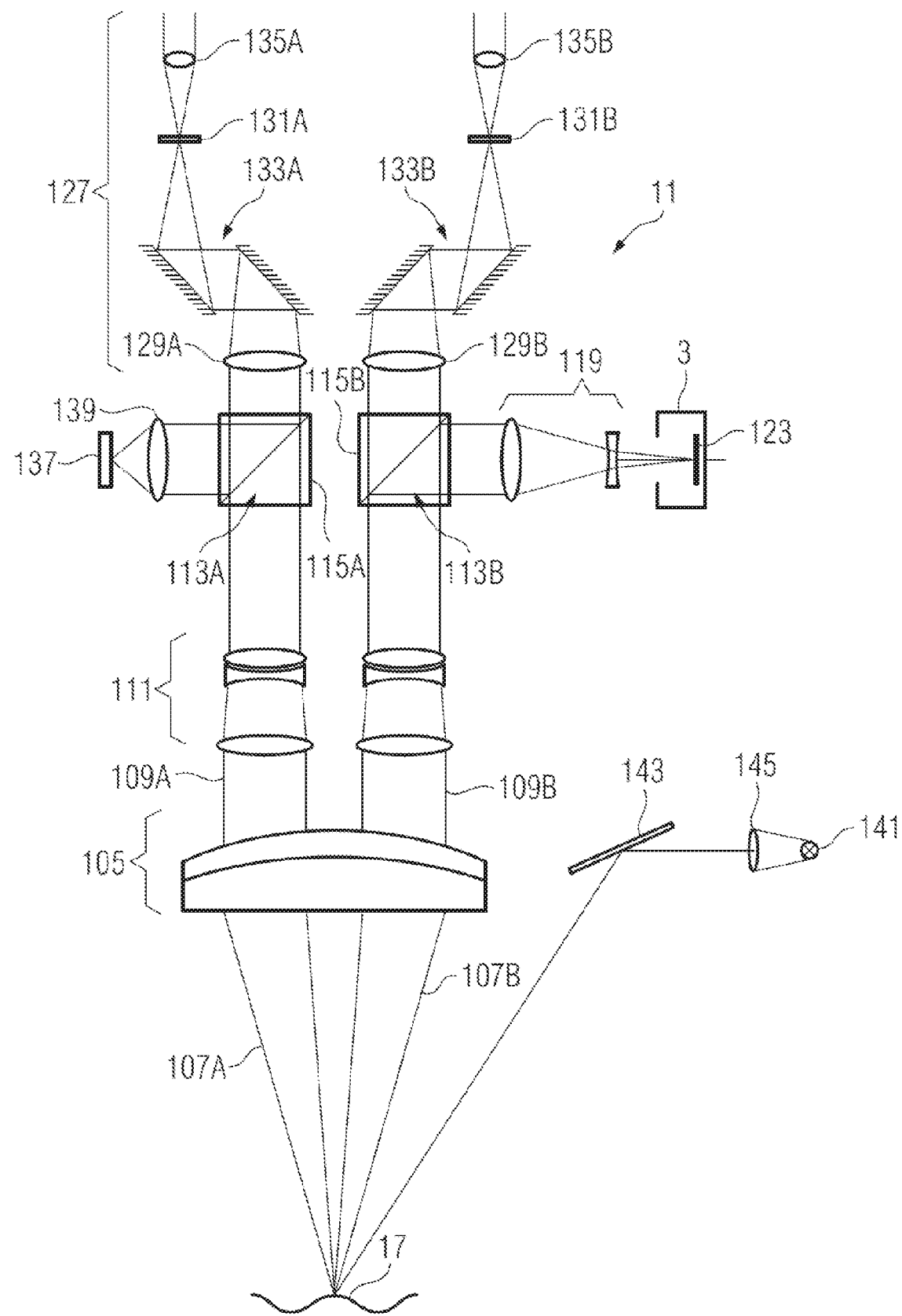
FIG. 2 shows the set-up of a surgical microscope in a schematic illustration.
Figure 3:
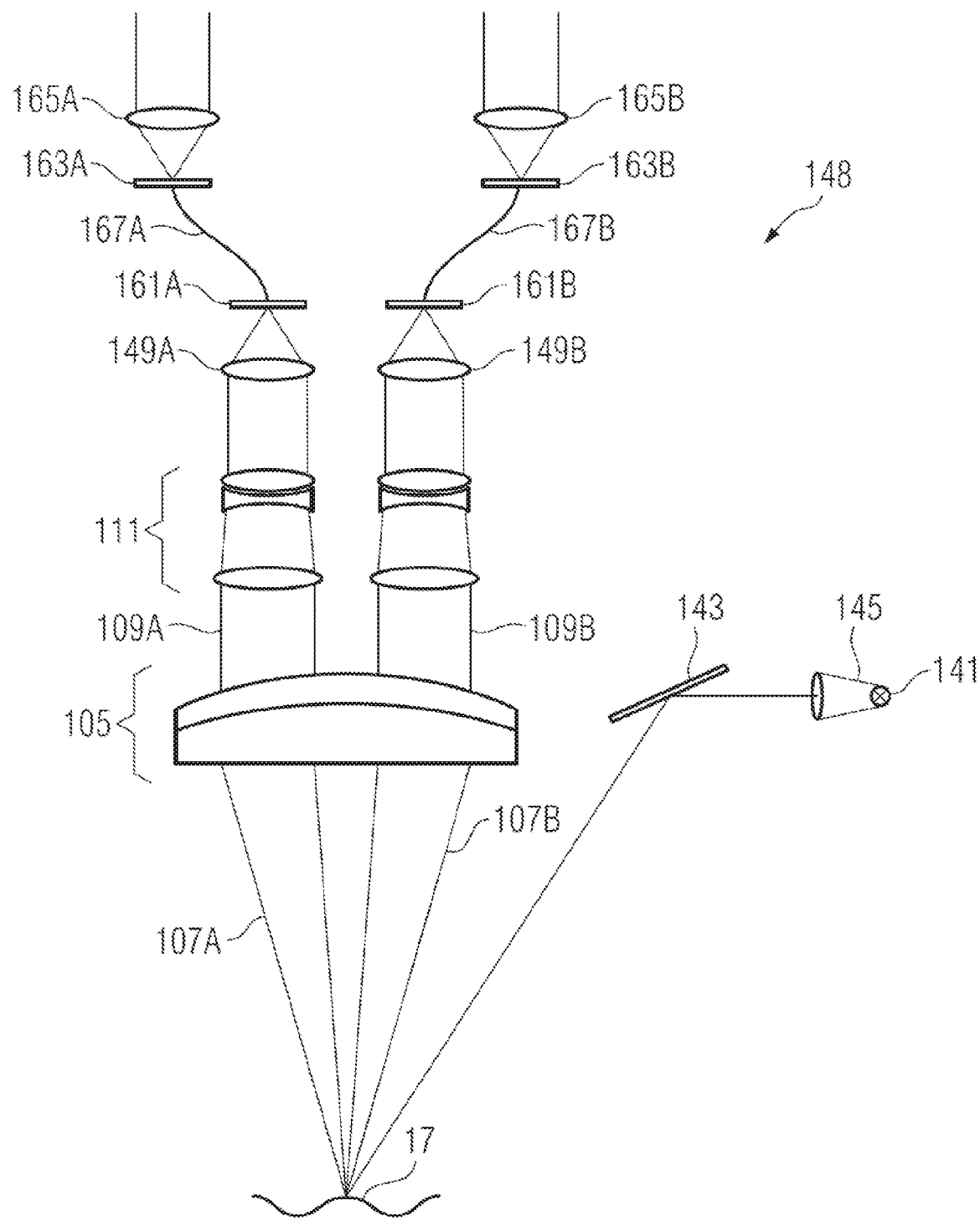
FIG. 3 shows an alternative configuration of the surgical microscope.
Figure 4:
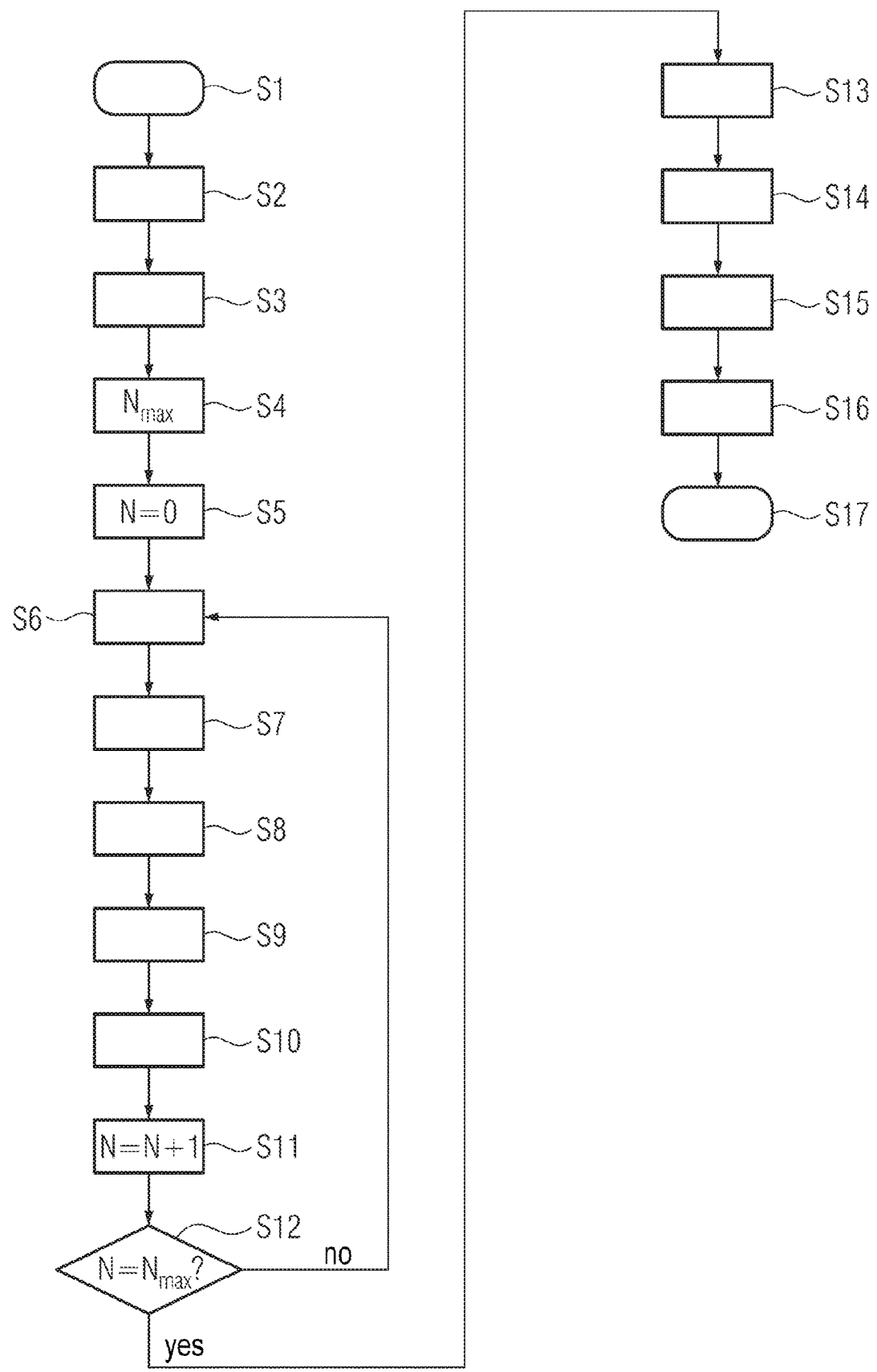
FIG. 4 shows a flow diagram for a method for creating and displaying a map of a brain operating field; and, FIG. 5 shows a monitor view with maps of a brain operating field.

Exemplary embodiments are described below with reference to FIGS. 1 to 5. In this case, FIG. 1 shows an embodiment of a device for creating and displaying a map of a brain operating field, and FIG. 4 shows an embodiment of the method for creating and displaying a map of a brain operating field. FIGS. 2 and 3 show examples of the set-up of surgical microscopes such as can be used in the context of the device shown in FIG. 1.

In accordance with the embodiment of the device for creating and displaying a map of a brain operating field 17, as shown in FIG. 1, the device includes a stimulation device in the form of a nerve stimulator 1, a recording device in the form of a camera 3, a display device in the form of a monitor 5 and a control and evaluation device 7, which is connected to the nerve stimulator 1, the camera 3 and the monitor 5.

In the present embodiment, the nerve stimulator 1 is configured for electrically stimulating nerves. For this purpose, it includes a number of electrodes 9, which can be used to electrically stimulate nerves of the peripheral nervous system such as, for example, the median nerve (Nervus medianus), which is responsible for the motor control of the forearm muscles and some finger muscles and for the sensitive innervation of the palm and the thumb as far as the inner side of the ring finger, or the trigeminal nerve, which is responsible for sensation in the face and for the motor functions of the face, oral cavity and muscles of mastication. The control and evaluation device 7 serves for controlling the stimulation.

In the present embodiment, the camera 3 is part of a surgical microscope 11. Surgical microscopes generally include a camera for documentation purposes, which camera can be used for recording stimulation images and reference images during an intraoperative optical imaging process. The camera 3 has an electronic image sensor and is controlled by the control and evaluation device 7. In addition, digital images recorded by an electronic camera chip of the camera 3 are output to the control and evaluation device 7.

The control and evaluation device 7 is illustrated as an independent unit in FIG. 1. A person skilled in the art recognizes, however, that the control and evaluation device 7 need not necessarily be an independent unit. In particular, the control and evaluation device 7 can also be integrated in the control unit of a surgical microscope. If by contrast, as illustrated in FIG. 1, the control and evaluation device 7 is an independent unit, it can be formed by a commercially available PC, for example, on which a suitable computer program runs. The control and evaluation device 7 typically includes in all cases a processor and a memory for storing programs which can be executed with the aid of the processor.

In addition to controlling the nerve stimulator 1 and the camera 3, the control and evaluation device 7 is also responsible for creating a map of the brain operating field 17 from the stimulation images and reference images recorded with the aid of the camera 3, brain tissue areas 15 associated with at least one stimulated brain function being marked in the map. The maps created by the control and evaluation device 7 are then output to the monitor 5 in order to be displayed thereon.

FIG. 1 shows highly schematically a map 13 displayed on the monitor 5, an activated brain tissue area 15 associated with a stimulated brain function being marked in the map. The marking, which is illustrated by a hatching in FIG. 1, can be effected for example by coloration of the brain tissue area associated with the stimulated brain function, by placing a border around the brain tissue area associated with the stimulated brain function, by reducing the color saturation of brain tissue areas located outside the brain tissue area associated with the stimulated brain function, et cetera. If different brain tissue areas associated with different stimulated brain functions are intended to be marked in the map 13, this can be done by different coloration, for example. In principle, it is possible, instead of a color differentiation of brain tissue areas assigned to different brain functions, to identify the different tissue areas differentiably in some other way, for example by a brain tissue area associated with a first brain function being colored and a border being placed around a second brain tissue area associated with a second brain function. If the differentiation between the brain functions does not matter rather what matters is only whether a certain brain tissue area is associated with one of the stimulated brain functions, the marking can, however, also be effected with the same color. In principle, in the context of the present disclosure, any representation is possible which is suitable for differentiating the brain tissue areas associated with the stimulated brain functions from those which are not associated with the stimulated brain functions.

Besides the current map 13, further elements can be displayed on the monitor 5, for example previously created maps 13', 13" and/or quality parameters 16 assigned to the maps or the like.

The control and evaluation device 7 controls the nerve stimulator 1 and the camera 3 in such a way that during a measurement cycle in which at least one brain function is stimulated, at least one stimulation image of the brain operating field 17, that is, an image containing an optical signal caused by the stimulation, and at least one reference image, that is, an image not containing an optical signal caused by the stimulation, are recorded. In the present embodiment, at least one video sequence of the brain operating field 17 is recorded by the camera 3 during an intraoperative optical imaging process. The stimulation images and the reference images are then frames of the video sequence. During a measurement cycle carried out in the context of the intraoperative optical imaging process, a phase of the stimulation of a specific brain function with the aid of the nerve stimulator 1, called stimulation phase, and a phase without stimulation of the brain function, called rest phase, are effected successively.

A number of measurement cycles are strung together in the context of the intraoperative optical imaging process, such that rest phases and stimulation phases alternate over a specific period of time. By way of example, it is possible to use measurement cycles as described in M. Oelschlagel et al., that is, 30-second stimulation phases and 30-second rest phases alternating over 9 min. In the present embodiment example, the intraoperative optical imaging process includes a total of 9 stimulation phases and 9 rest phases, which can ultimately be used to create the map 13. However, the intraoperative optical imaging process can also include more or fewer than 9 measurement cycles. Moreover, the duration of the stimulation phases and of the rest phases can be longer or shorter than 30 seconds.

According to the disclosure, the control and evaluation device 7 controls the nerve stimulator 1 and the camera 3 in such a way that a plurality of measurement cycles are carried out, but at least two measurement cycles are carried out, and that a new, that is, updated, map 13 of the brain operating field 17 is created after each measurement cycle following the first measurement cycle. In order to create the new map, besides the stimulation images and reference images recorded in the measurement cycle just concluded, the control and evaluation device 7 then also uses the stimulation images and reference images of at least one preceding measurement cycle. After each measurement cycle of the intraoperative optical imaging process, the control and evaluation device 7 additionally updates the representation on the monitor 5 in such a way that at least the map 13 created after the measurement cycle just concluded is displayed. Typically, however, at least one of the previously created maps 13', 13", typically at least the map created before the current map 13, is also displayed, provided that at least one previously created map is present.

In the present embodiment, the maps 13, 13', 13" of the brain operating field 17 are displayed on the monitor 5 together with quality parameters 16, 16', 16" assigned to them, wherein a quality parameter represents a measure of the disturbances that occurred in the stimulation and reference images used for creating the respective map. Locally delimited disturbances such as reflections or bleeding, for instance, can additionally or alternatively also be depicted in the respective maps 13, 13', 13".

In the embodiment shown in FIG. 1, the camera 3 is integrated in a surgical microscope 11. However, the camera 3 need not be integrated in a surgical microscope, and so the presence of a surgical microscope 11 as part of the device is not absolutely necessary.

FIG. 2 shows, in a schematic illustration, a possible set-up of the surgical microscope 11 such as can be used in the device from FIG. 1. FIG. 3 shows a possible alternative set-up.

The surgical microscope 11 shown in FIG. 2 includes, as essential components, an objective 105 that is to face an object field 17, which is the brain operating field 17 in the present embodiment, which objective 105 can be embodied in particular as an achromatic or apochromatic objective. In the present embodiment, the objective 105 includes two partial lenses that are cemented to one another and form an achromatic objective. The object field 17 is arranged in the focal plane of the objective 105 such that it is imaged at infinity by the objective 105. Expressed differently, a divergent beam 107A, 107B emanating from the object field 3 is converted into a parallel beam 109A, 109B during its passage through the objective 105.

A magnification changer 111 is arranged on the observer side of the objective 105, which magnification changer can be embodied either as a zoom system for changing the magnification factor in a continuously variable manner as in the illustrated embodiment, or as what is known as a Galilean changer for changing the magnification factor in a stepwise manner. In a zoom system, constructed by way of example from a lens combination having three lenses, the two object-side lenses can be displaced in order to vary the magnification factor. In actual fact, however, the zoom system also can have more than three lenses, for example four or more lenses, in which case the outer lenses then can also be arranged in a fixed manner. In a Galilean changer, by contrast, there are a plurality of fixed lens combinations which represent different magnification factors and which can be introduced into the beam path alternately. Both a zoom system and a Galilean changer convert an object-side parallel beam into an observer-side parallel beam having a different beam diameter. In the present embodiment, the magnification changer 111 is already part of the binocular beam path of the surgical microscope 11, that is, it has a dedicated lens combination for each stereoscopic partial beam path 109A, 109B of the surgical microscope 11. In the present embodiment, a magnification factor is set via the magnification changer 111 by way of a motor-driven actuator which, together with the magnification changer 111, is part of a magnification changing unit for setting the magnification factor.

The magnification changer 111 is followed on the observer side by an interface arrangement 113A, 113B, via which external apparatuses can be connected to the surgical microscope 11 and which includes beam splitter prisms 115A, 115B in the present embodiment. However, in principle, use can also be made of other types of beam splitters, for example partly transmissive mirrors. In the present embodiment, the interfaces 113A, 113B serve to output couple a beam from the beam path of the surgical microscope 11 (beam splitter prism 115B) and to input couple a beam into the beam path of the surgical microscope 11 (beam splitter prism 115A).

In the present embodiment, the beam splitter prism 115A in the partial beam path 109A serves to reflect information or data for an observer into the partial beam path 109A of the surgical microscope 1 with the aid of a display 137, for example a digital mirror device (DMD) or an LCD display, and an associated optical unit 139 by way of the beam splitter prism 115A. During a brain operation, it is possible to reflect in, for example, a map 13 of a brain operating field, brain tissue areas 15 associated with at least one stimulated brain function being marked in the map. A camera adapter 119 with a camera 3 secured thereto, the camera being equipped with an electronic image sensor 123, for example with a CCD sensor or a CMOS sensor, is arranged at the interface 113B in the other partial beam path 109B. It is possible via the camera 3 to record an electronic image and, in particular, a digital image of the object field 17. The image sensor used can also be, in particular, a hyperspectral sensor including not just three spectral channels (for example, red, green and blue), but rather a multiplicity of spectral channels. In the embodiment as shown in FIG. 1, the video sequences containing the stimulation images and reference images are recorded by the camera 3.

The interface 113A, 113B is followed on the observer side by a binocular tube 127. The latter has two tube objectives 129A, 129B, which focus the respective parallel beam 109A, 109B onto an intermediate image plane 131, that is, image the object field 17 onto the respective intermediate image plane 131A, 131B. The intermediate images situated in the intermediate image planes 131A, 131B are finally imaged at infinity in turn by eyepiece lenses 135A, 135B, such that an observer can observe the intermediate image with a relaxed eye. Moreover, an increase in the distance between the two partial beams 109A, 109B is implemented in the binocular tube via a mirror system or via prisms 133A, 133B in order to adapt the distance to the interocular distance of the observer. In addition, image erection is carried out by the mirror system or the prisms 133A, 133B.

The surgical microscope 11 is additionally equipped with an illumination device, via which the object field 17 can be illuminated with broadband illumination light. For this purpose, in the present embodiment, the illumination device includes a white light source 141, for instance a halogen incandescent lamp or a gas discharge lamp. The light emanating from the white light source 141 is directed in the direction of the object field 17 via a deflection mirror 143 or a deflection prism in order to illuminate the field. Furthermore, an illumination optical unit 145 is present in the illumination device, the illumination optical unit ensuring uniform illumination of the entire observed object field 17.

It should be pointed out that the illumination beam path illustrated in FIG. 2 is highly schematic and does not necessarily reproduce the actual course of the illumination beam path. In principle, the illumination beam path can be embodied as so-called oblique illumination, which comes closest to the schematic illustration in FIG. 2. In such oblique illumination, the beam path extends at a relatively large angle (6° or more) with respect to the optical axis of the objective 105 and, as illustrated in FIG. 2, may extend completely outside the objective. Alternatively, however, there is also the possibility of allowing the illumination beam path of the oblique illumination to extend through a marginal region of the objective 105. A further possibility for the arrangement of the illumination beam path is what is known as 0° illumination, in which the illumination beam path extends through the objective 105 and is coupled into the objective 105 between the two partial beam paths 109A, 109B, along the optical axis of the objective 105 in the direction of the object field 17. Finally, it is also possible to embody the illumination beam path as so-called coaxial illumination, in which a first illumination partial beam path and a second illumination partial beam path are present. The partial beam paths are coupled into the surgical microscope 11 via one or more beam splitters parallel to the optical axes of the observation partial beam paths 109A, 109B, such that the illumination extends coaxially with respect to the two observation partial beam paths.

The illumination can be influenced in the surgical microscope 11 illustrated in FIG. 2. By way of example, a filter can be introduced into the illumination beam path, the filter transmitting only a narrow spectral range from the wide spectrum of the white light source 141, for example, a spectral range that enables the excitation of fluorescence of a fluorescent dye situated in the object field 17. In order to observe the fluorescence, filters 137A, 137B can be introduced into the observation partial beam paths, the filters filtering out the spectral range used for excitation of fluorescence, in order to be able to observe the fluorescence. In the present embodiment, in the course of recording the stimulation images and the reference images, a filter can be introduced into the illumination beam path, the filter transmitting only those wavelength ranges of the illumination light in which a change in the perfusion or a change in the oxygen content of the blood generates a particularly distinct signal in the observation beam path.

In the embodiment variant of the surgical microscope 11 shown in FIG. 2, the objective 105 includes only one achromatic lens. However, use can also be made of an objective lens system composed of a plurality of lenses, in particular a so-called varioscope objective, with which it is possible to vary the working distance of the surgical microscope 11, that is, the distance between the object-side focal plane and the vertex of the first object-side lens surface of the objective 105, also referred to as front focal distance. The object field 17 arranged in the focal plane is imaged at infinity by a varioscope objective, too, and so a parallel beam is present on the observer side.

FIG. 3 shows one example of a digital surgical microscope 148 in a schematic illustration. In this surgical microscope, the main objective 105, the magnification changer 111 and the illumination system 141, 143, 145 do not differ from the surgical microscope 11 with the optical view that is illustrated in FIG. 2. The difference lies in the fact that the surgical microscope 148 shown in FIG. 3 does not include an optical binocular tube. Instead of the tube objectives 129A, 129B from FIG. 2, the surgical microscope 148 from FIG. 3 includes focusing lenses 149A, 149B, with which the binocular observation beam paths 109A, 109B are imaged on digital image sensors 161A, 161B. Here, the digital image sensors 161A, 161B can be, for example, CCD sensors or CMOS sensors. The images recorded by the image sensors 161A, 161B are transmitted digitally to digital displays 163A, 163B, which may be embodied as LED displays, as LCD displays or as displays based on organic light-emitting diodes (OLEDs). As in the present example, eyepiece lenses 165A, 165B can be assigned to the displays 163A, 163B, with which lenses the images displayed on the displays 163A, 163B are imaged at infinity such that an observer can observe the images with relaxed eyes. The displays 163A, 163B and the eyepiece lenses 165A, 165B can be part of a digital binocular tube; however, they can also be part of a head mounted display (HMD) such as, for example, a pair of smartglasses.

In the embodiment as shown in FIG. 1, the video sequences containing the stimulation images and reference images can be recorded by at least one of the digital image sensors 161A, 161B. In this case, the digital image sensor or the digital image sensors constitute(s) the imaging device from FIG. 1.

Even though FIG. 3, like FIG. 2, only illustrates one achromatic lens 105 with a fixed focal length, the surgical microscope 148 shown in FIG. 3 may include a varioscope objective instead of the objective lens 105, like the surgical microscope 11 illustrated in FIG. 2. Furthermore, FIG. 3 shows a transfer of the images recorded by the image sensors 161A, 161B to the displays 163A, 163B via cables 167A, 167B. Instead of being transferred in a cable-based manner, however, the images can also be transferred wirelessly to the displays 163A, 163B, particularly if the displays 163A, 163B are part of a head mounted display.

One embodiment of the method for creating and displaying a map of a brain operating field 17 is described below with reference to FIG. 4. The method steps illustrated in FIG. 4 are carried out by the control and evaluation device 7 illustrated in FIG. 1, or, insofar as external apparatuses such as the nerve stimulator 1, the camera 3 and the monitor 5 are required for carrying out method steps, these external devices are controlled by the control and evaluation device 7 by way of corresponding signals.

Before the beginning of the method, the surgical microscope 11 with the camera 3 arranged therein is aligned with and focused on the brain operating field 17. Afterward, the method is started (S1). After the start, the set apparatus parameters of the surgical microscope 11 are displayed in step S2. Examples of appropriate apparatus parameters are the focal length of the surgical microscope, the illumination intensity, the color of the illumination light, the magnification setting of the magnification changer, et cetera. With the aid of the display, the user of the device can check the parameters set and, if appropriate, make changes. With the set apparatus parameters, in step S3, on the basis of the image captured by the camera 3, a check is made to ascertain whether the image of the brain operating field 17 obtained with the set apparatus parameters is suitable for carrying out the method. For this purpose, in the present embodiment, the following steps are carried out:

Recording a color image of the brain operating field 17, determining whether the brain operating field 17 is at the focus of the surgical microscope, creating a focus indicator indicating whether and to what extent the brain operating field 17 is at a distance from the focus of the surgical microscope 11, and displaying the focus indicator on the monitor 5.

Ascertaining the illumination quality, in this case in particular the illumination intensity and the color of the illumination light, creating an illumination indicator forming a measure of the illumination quality, and displaying the illumination indicator on the monitor 5.

Determining illumination reflections in the image of the brain operating field 17 and determining whether critical illumination reflections are present, that is, illumination reflections which reduce the identifiability of brain areas to an extent such that it is not possible to detect brain activity associated with stimulations, creating a reflection indicator and displaying the reflection indicator on the monitor 5. In this case, the reflection indicator can for example mark critical reflections directly in the image of the brain operating field 17. Alternatively or additionally, it can indicate the magnitude of the proportion of brain areas with critical reflections in the total brain area of the brain operating field 17.

Determining whether bleeding can be discerned in the recorded image, creating a bleeding indicator and displaying the bleeding indicator on the monitor 5. In this case, the bleeding indicator can indicate for example the magnitude of the proportion of brain areas masked by bleeding in the total brain area of the brain operating region.

Determining the magnification setting (zoom) of the surgical microscope 11, creating a zoom indicator and displaying the zoom indicator on the monitor 5. The zoom indicator can indicate the magnification factor in the form of a numerical value, for example.

Determining the edge of the brain operating field 17, determining how far the optical axis of the surgical microscope 11 deviates from the center of the brain operating field 17, that is, the extent to which the optical axis of the surgical microscope 11 is decentered relative to the center of the brain operating field 17, determining a centration indicator indicating the degree of decentration and displaying the decentration indicator on the monitor 5.

With the aid of the indicators displayed on the monitor 5, the user then has the possibility either of varying apparatus parameters or the positioning of the surgical microscope, should this be necessary, or of beginning the implementation of the intraoperative optical imaging process. In the latter case, the user can predefine (step S4) a maximum number $N_{max}$ of stimulation cycles carried out in the context of the intraoperative optical imaging process. Alternatively, there is also the possibility of fixedly predefining a maximum number $N_{max}$ of stimulation cycles, which either cannot be altered or is used if the user does not input a deviating maximum number of stimulation cycles in step S4. In the next step, a counter value N indicating how many stimulation cycles have already been carried out is set to zero (S5). Step S6 involves initiating the implementation of a measurement cycle.

In the present embodiment, a measurement cycle includes in each case a 30-second stimulation phase and a 30-second rest phase. During the measurement cycles, a video of the brain operating field 17 is recorded (step S7) by the camera 3, the video being evaluated in step S8. In the context of the evaluation, for the pixels of the frames of the video sequence, a frequency spectrum of the pixel intensity in a specific wavelength range is created, preferably in the green/blue wavelength range, and those pixels are determined which have an intensity variation whose frequency corresponds to that frequency at which the stimulation cycles succeed one another. Such intensity variations are a signal that the pixel in the image lies in a region showing brain tissue areas 15 associated with the stimulated brain function. The totality of such pixels then represents the brain tissue areas associated with the stimulated brain function. In order to prevent noise from being regarded as a signal, a threshold value for the amplitude of the intensity variations of a pixel can be predefined, which threshold value must be exceeded in order that the intensity variation is regarded as a signal that the pixel in the image lies in a region showing brain tissue areas 15 associated with the stimulated brain function. In this case, the threshold value should be above the noise amplitude.

If the measurement cycle implemented is the first measurement cycle, an intensity fluctuation varying with the frequency of the measurement cycles cannot as yet be established from the recorded video since this necessitates at least two measurement cycles. Therefore, the first evaluation will not yet find any pixels that could be assigned to activated brain tissue areas.

The next step (S9) involves creating a map 13 on the basis of the evaluation carried out in step S8, the map marking the brain tissue areas 15 associated with the stimulated brain function. Creating the map 13 can be effected for example by creating a still image from the recorded video sequence and marking in color in the still image those pixels which represent the brain tissue area activated by the stimulation. Instead of a color marking, other markings are also possible, for example by placing a border around the corresponding brain tissue area, a marking by increasing the image brightness for the pixels representing the brain tissue area, reducing the image brightness or the color saturation of the brain tissue areas 15 not associated with the stimulation et cetera. The still image can be created either by a single frame being selected from the frames or by the frames being superimposed on one another. The map 13 created after the first measurement cycle does not yet contain any markings, however, since in step S8 the data situation is not yet sufficient to determine such brain tissue areas 15.

Step S9 involves checking the recorded video sequence for disturbances that may adversely affect the process of finding the brain tissue areas 15 activated with the aid of the stimulation. Such disturbances may be, for example, bleeding that masks parts of the brain tissue area to be identified in the brain operating field 17, reflections that hamper the identifiability of brain tissue areas in the brain operating field 17, maskings of the brain operating field 17 by instruments projecting into the image field, et cetera. In the present embodiment, the disturbances are displayed (S10) together with the created map 13 of the brain operating field on the monitor 5. In this case, the disturbance can be displayed directly in map 13, for example by the regions with disturbances being marked in color, enclosed by a border, darkened, et cetera. Additionally or alternatively, there is a possibility of determining and outputting a quality parameter. The quality parameter can be, for example, a numerical value indicating the magnitude of the proportion of the brain tissue area affected by the disturbances in the total brain tissue area visible in the brain operating field 17. In step S10 in the context of the present embodiment, the current counter value N indicating which number measurement cycle is taken as a basis for the displayed map is also displayed on the monitor 5. In the next step, step S11, the counter value N is then increased by 1 to the counter value N+1.

Step S12 then involves interrogating whether the counter reading N has already reached the value $N_{max}$ representing the maximum number of measurement cycles. If this is not the case, the method returns to step S6 and initiates the next measurement cycle. Starting from the second measurement cycle it is possible, in principle, to find pixels whose intensity fluctuates with the period of the measurement cycles, provided that the signal is strong enough, that is, the amplitude of the fluctuation is greater than the noise amplitude of the frequency spectrum. As the number of measurement cycles increases, the signal-to-noise ratio improves, such that better maps 13—that is, maps with less noise—of the brain tissue areas 15 associated with the stimulated function should be expected as the number of measurement cycles increases.

Starting from the second measurement cycle, the video sequences of all preceding measurement cycles are also used for creating the most up-to-date map, in order to obtain the best possible signal-to-noise ratio. After each measurement cycle, therefore, a new map 13 is created which is based both on the video sequences of the measurement cycle just carried out and on the video sequences of all preceding measurement cycles. In step S10, this newly created map 13 is displayed together with a number of maps 13', 13" created after preceding measurement cycles on the monitor 5. In the present embodiment, in addition to the current newly created map, all previously created maps 13', 13" are also displayed on the monitor 5. Moreover, in each of the displayed maps 13, 13', 13", the disturbances that occurred in the video sequences on which the respective map is based are also displayed together with the quality parameter 16, 16', 16" determined from the disturbances.

If the sequence of the displayed maps 13, 13', 13" reveals that a map of sufficient quality should not be expected even with the predefined number $N_{max}$ of measurement cycles, the user can end the intraoperative optical imaging process prematurely, if possible eliminate the disturbances and then restart the intraoperative optical imaging process. Disturbances can be eliminated for example by changing the position of the surgical microscope and/or the illumination parameters, by staunching bleeding, et cetera.

On the other hand, if a map 13 of sufficient quality indicating the brain tissue areas 15 activated by the stimulation is already present before the maximum number of measurement cycles is reached, the user can likewise end the implementation of the intraoperative optical imaging process prematurely and carry out or continue the brain operation on the basis of the map 13 created up until then.

In both cases, prematurely ending the intraoperative optical imaging process results in a time gain by comparison with the intraoperative optical imaging processes known from the prior art, since the intraoperative optical imagining process does not have to be finished first before the intraoperative optical imaging process can be restarted with new parameters or the brain operation can be carried out or continued.

Figure 5:
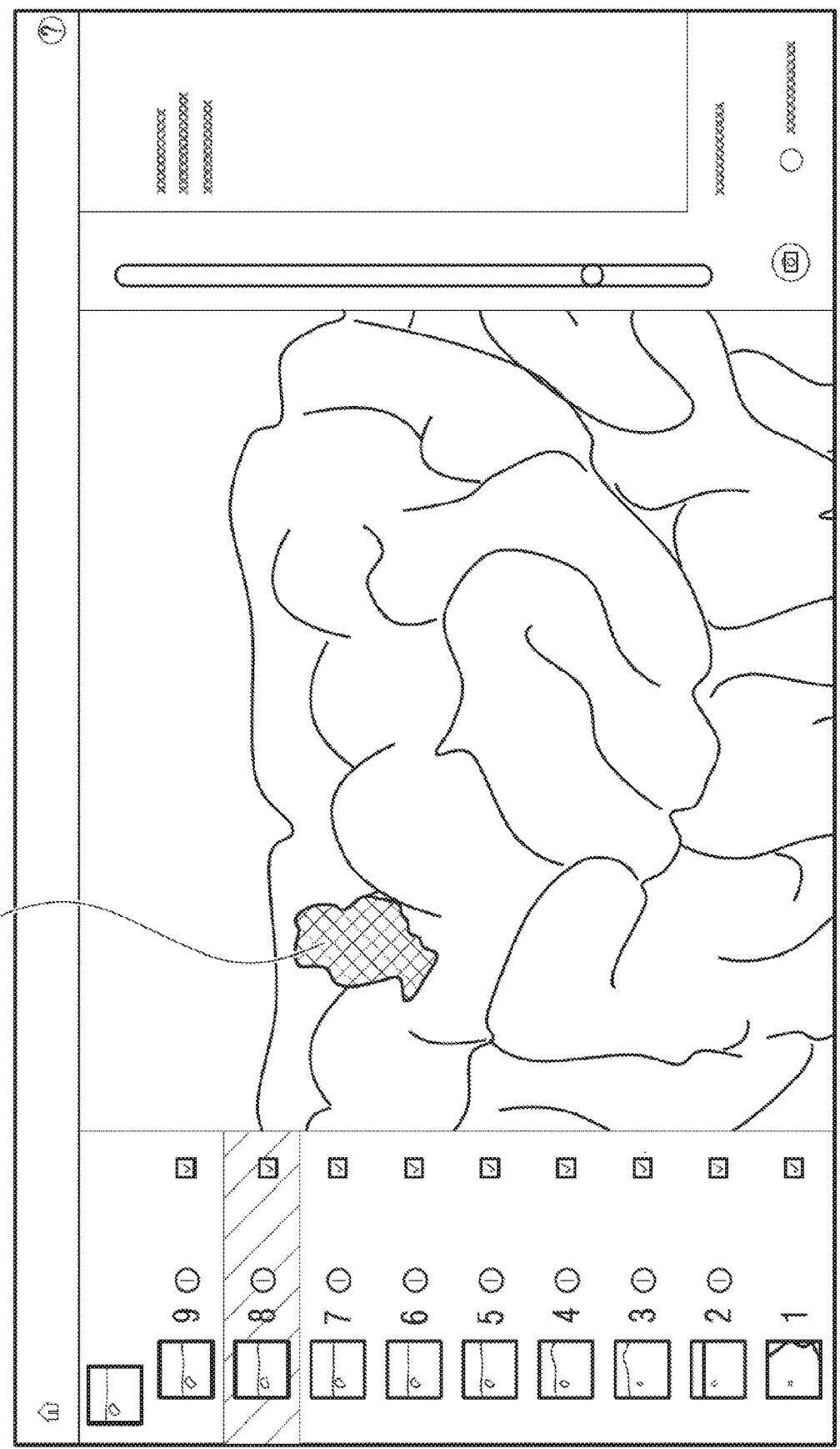

If it is established in step S12 that the maximum number of measurement cycles $N_{max}$ has been reached, the method advances to step S13, in which each map 13', 13" created after a measurement cycle together with the map 13 representing the end result are displayed on the monitor. One possible representation is shown in FIG. 5. In the present embodiment, the ninth map represents the end result. The map is displayed in a large manner on the monitor 5, while the maps of the measurement cycles 1 to 9 are displayed with reduced size in the column on the left. The user then has the possibility, by clicking on one of the maps 1 to 9, of enabling the respective map, instead of the map 13 forming the end result, to be displayed in a large manner on the monitor 5, in order to check to what extent the map is affected by disturbances. FIG. 5 shows a monitor view in which map no. 8 is displayed in an enlarged manner. An area 19 with a disturbance, namely a strong reflection, is displayed therein. Since this disturbance is not present or is hardly present in maps 1 to 7, it can be deduced that the cause of the disturbance is present in the video sequences of the eighth measurement cycle. Since the disturbance has also not become smaller again in the ninth measurement cycle, it can additionally be assumed that the disturbance is still present in the video sequences of the ninth measurement cycle as well. If the disturbance were smaller in the ninth map than in the eighth map, it could be assumed that the disturbance is no longer present, or at least no longer present as seriously, in the video sequences of the ninth measurement cycle. In the present example, therefore, the eighth and ninth measurement cycles are sorted out (step S14), for example, by removing a check mark set as standard on the maps created after these measurement cycles, or by some other marking of the measurement cycles to be sorted out, and the map forming the end result is created anew (step S15) on the basis of the measurement cycles 1 to 7 and is displayed together with the maps 1 to 9 on the monitor 5, wherein the maps 8 and 9 are assigned a marking indicating that the measurement cycles 8 and 9 have been sorted out (step S16). The map forming the end result then substantially corresponds to the map created after measurement cycle no. 7. If the disturbance were discernible less distinctly in the map created after the ninth measurement cycle and it could therefore be assumed that the disturbance is no longer present, or is present at least to a greatly reduced extent, in the video sequences of the ninth measurement cycle, only the eighth measurement cycle could be sorted out and the map forming the end result could be created anew on the basis of the video sequences of measurement cycles 1 to 7 and 9. In this case, the map forming the end result would not correspond to any of the previously created maps.

Upon displaying all maps and the resulting map or optionally creating anew the resulting map after sorting out measurement cycles, the method is ended (S17).

Insofar as the individual method steps of the method illustrated in FIG. 4 can be carried out on a data processing device such as a PC or the control unit of a surgical microscope 11, the method steps can be present in the form of instructions of a computer program which can be loaded into the data processing device in order to enable the method to be carried out. The computer program can be stored on a nontransitory computer-readable storage medium, for example a DVD, a USB stick, a floppy disk, et cetera, or else be provided for retrieval in a network such as, for example, a local area network (LAN) or a wide area network (WAN) such as the Internet, for example.

The present invention has been described in detail on the basis of exemplary embodiments for the purposes of explanation. However, a person skilled in the art recognizes that it is also possible to depart from the concrete exemplary embodiments in the context of the invention, as has already been mentioned in the context of the description of the exemplary embodiments. Therefore, the scope of protection of the invention is not intended to be restricted by the exemplary embodiments, but rather only by the appended claims.

LIST OF REFERENCE NUMERALS

1 Nerve stimulator
3 Camera
5 Monitor
7 Control and evaluation device
9 Electrode
11 Surgical microscope
13 Map
15 Brain tissue area associated with stimulated brain function
16 Quality parameter
17 Brain operating field
19 Area with disturbance
105 Objective
107A,B Divergent beam
109A,B Parallel/partial beam
111 Magnification changer
113A,B Interface arrangement
115A,B Beam splitter prism
119 Camera adapter
123 Image sensor
127 Binocular tube
129A,B Tube objective
131A,B Intermediate image plane
133A,B Prism
135A,B Eyepiece lens
137 Display
139 Optical unit
137A, 137B Filters
141 White light source
143 Deflection mirror
145 Illumination optical unit
148 Surgical microscope
149 A,B Focusing lens
161 A,B Image sensor
163 A,B Display
165 A,B Eyepiece lens
167 A,B Cable
S1 Start
S2 Displaying the set apparatus parameters
S3 Checking whether the image obtained is suitable
S4 Predefining the maximum number $N_{max}$ of stimulation cycles
S5 Setting counter value N=0
S6 Initiating implementation of a measurement cycle
S7 Recording a video of the brain operating field
S8 Evaluating
S9 Creating a map
S10 Displaying the map on the monitor
S11 Increasing counter value to N+1
S12 Interrogating whether $N=N_{max}$
S13 Displaying each created map and the map representing the end result S14 Optionally sorting out measurement cycles
S15 Creating anew the map representing the end result
S16 Displaying the newly created map
S17 End

What is claimed is:

1. A method for intraoperatively generating and displaying a map of a brain operating field with brain tissue areas associated with at least one stimulated brain function being marked in said map, the method comprising:
performing a plurality of measurement cycles including a first measurement cycle, each of the plurality of measurement cycles including
effecting a stimulation of at least one brain function,
recording at least one stimulation image of the brain operating field with the stimulated at least one brain function,
recording at least one reference image of the brain operating field without the at least one stimulated brain function,
generating a map using the at least one stimulation image recorded in the measurement cycle and the at least one reference image, and
displaying the map on a display device;
generating a new map of the brain operating field after each one of the plurality of measurement cycles following a first measurement cycle, wherein, in order to generate the new map, the at least one stimulation image and the at least one reference image of one or more preceding measurement cycles are used in addition to the at least one stimulation image recorded in the measurement cycle just carried out and the at least one reference image recorded in the measurement cycle just carried out, and at least the new map generated after the measurement cycle just carried out is displayed after each measurement cycle;
examining the at least one stimulation image and the at least one reference image used for said generating the new map for disturbances;
determining a numerical value representing a measure of the disturbances in the at least one stimulation image and the at least one reference image used for said generating the new map as a quality parameter;
assigning the quality parameter to the new map;
displaying the quality parameter beside the new map; and
wherein the numerical value indicates a magnitude of a proportion of the brain tissue area affected by the disturbances in a total brain tissue area visible in the brain operating field.

2. The method of claim 1, wherein, after each measurement cycle following the first measurement cycle, at least that map which was generated before the map generated after the measurement cycle just carried out is also displayed.

3. The method of claim 1, wherein, during the measurement cycle, a plurality of stimulation images and reference images are recorded and, from each measurement cycle, the plurality of recorded stimulation images and reference images are used for generating the map of the brain operating field.

4. The method of claim 1, wherein a maximum number ($N_{max}$) of measurement cycles is predefinable and the number (N) of the measurement cycle after which the respective map was generated is also displayed besides the map or the maps.

5. The method of claim 4, wherein there is a possibility of terminating said generating of maps before reaching the maximum number ($N_{max}$) of measurement cycles.

6. The method of claim 1 further comprising:
examining the at least one stimulation image and the at least one reference image used for generating the map for disturbances; and,
displaying, in addition to said map, at least one of the disturbances that occurred in the at least one stimulation image and the at least one reference image used to generate said map and a quality parameter in addition to said map, wherein the quality parameter represents a measure of the disturbances that occurred in the at least one simulation image and the at least one reference image used to generate said map.

7. The method of claim 6, wherein, after the end of all the measurement cycles, each map generated after a measurement cycle together with the disturbances that occurred in the at least one stimulation image and the at least one reference image used to generate said map, and/or together with the quality parameter assigned to the respective map, are displayed and a user is afforded the possibility of sorting out individual measurement cycles and of newly generating a new map on the basis of the stimulation images and reference images of the measurement cycles that have not been sorted out.

8. The method of claim 1 further comprising:
determining, before the first measurement cycle, indicators for parameters which are relevant to the stimulation and to the recording of the at least one stimulation image and the at least one reference image; and,
displaying the indicators determined.

9. A computer-implemented method for generating and displaying a map of a brain operating field, brain tissue areas associated with at least one stimulated brain function being marked in said map, the computer-implemented method comprising
generating control signals for controlling a stimulation device and a recording device in such a way that during each of a plurality of measurement cycles a stimulation of at least one brain function is effected and at least one stimulation image of the brain operating field with the stimulated brain function is recorded, and that during each of the measurement cycles at least one reference image of the brain operating field without the stimulated brain function is recorded, wherein the plurality of measurement cycles includes a first measurement cycle,
generating a map of the brain operating field using the at least one stimulation image recorded in the measurement cycle and the at least one reference image recorded in the measurement cycle, and
generating a signal for a display device and outputting the signal to the display device, wherein the signal has the effect that the map is displayed on the display device, generating the control signals for the stimulation device and the recording device in such a way that the plurality of measurement cycles are carried out and a new map of the brain operating field is generated after each one of the plurality of measurement cycles following the first measurement cycle, wherein, in order to generate the new map, the at least one stimulation image and the at least one reference image of one or more preceding measurement cycles are used in addition to the at least one stimulation image recorded in the measurement cycle just carried out and the at least one reference image recorded in the measurement cycle just carried out, and after each measurement cycle the signal for the display device is updated in such a way that at least the new map generated after the measurement cycle just carried out is displayed on the display device;

examining the at least one stimulation image and the at least one reference image used for said generating the new map for disturbances;

determining a numerical value representing a measure of the disturbances in the at least one stimulation image and the at least one reference image used for said generating the new map as a quality parameter;

assigning the quality parameter to the new map;

displaying the quality parameter beside the new map; and wherein the numerical value indicates a magnitude of a proportion of the brain tissue area affected by the disturbances in a total brain tissue area visible in the brain operating field.

10. The computer-implemented method of claim 9, wherein, after each measurement cycle following the first measurement cycle, the signal for the display device is updated in such a way that at least that map which was generated before the map generated after the measurement cycle just carried out is also displayed on the display device.

11. The computer-implemented method of claim 9, wherein the stimulation device and the recording device are controlled in such a way that a plurality of stimulation images and reference images are recorded during a measurement cycle; and, from each measurement cycle the plurality of recorded stimulation images and reference images are used for generating the map of the brain operating field.

12. The computer-implemented method of claim 9, wherein a maximum number ($N_{max}$) of measurement cycles is predefinable and the signal for the display device is generated in such a way that the number (N) of the measurement cycle after which a most up-to-date of the displayed maps was generated is also displayed besides the map or the maps on the display device.

13. The computer-implemented method of claim 12, wherein there is a possibility of terminating the generating of maps before reaching the maximum number ($N_{max}$) of measurement cycles.

14. The computer-implemented method of claim 9 further comprising examining the at least one stimulation image and the at least one reference image used for generating the map for disturbances; and, wherein the signal for the display device is generated in such a way that the disturbances that occurred in the at least one stimulation image and the at least one reference image on which the generated map is based are also displayed on the display device in addition to the generated map and/or a quality parameter assigned to the generated map is also displayed on the display device in addition to the generated map, the quality parameter representing a measure of the disturbances that occurred in the stimulation images and reference images on which the generated map is based.

15. The computer-implemented method of claim 14, wherein, after the end of all the measurement cycles, each map generated after a measurement cycle together with the disturbances that occurred in the at least one stimulation image and the at least one reference image on which the respective map is based, and/or together with the quality parameter assigned to the respective map, are displayed and a user is afforded the possibility of sorting out individual measurement cycles and of newly generating a new map on the basis of the stimulation images and reference images of the measurement cycles that have not been sorted out.

16. The computer-implemented method of claim 9, wherein the stimulation device and the recording device are controlled in such a way that, before the first measurement cycle, indicators are determined for parameters which are relevant to the stimulation and to the recording of the stimulation images and the reference images, and the indicators determined are displayed.

17. A computer program for supporting a surgeon during a brain operation, comprising instructions which, when they are executed on a computer, cause the computer to carry out the steps of the computer-implemented method as claimed in claim 9.

18. A data processing system for supporting a surgeon during a brain operation, wherein the data processing system comprises a processor and at least one memory and the processor is configured, on the basis of instructions of a computer program for supporting the surgeon during the brain operation, said computer program being stored in the memory, to carry out the steps of the computer-implemented method as claimed in claim 9 when executed by the processor.

19. A nontransitory computer-readable storage medium with instructions stored thereon for supporting a surgeon during a brain operation, wherein the instructions, when they are executed on a computer, cause the computer to carry out the steps of the computer-implemented method as claimed in claim 9.

20. A device for generating and displaying a map of a brain operating field, brain tissue areas associated with at least one stimulated brain function being marked in said map, the device comprising:

a stimulation device;

a recording device;

a display device;

a control and evaluation device connected or connectable to said stimulation device, said recording device, and said display device;

said control and evaluation device being configured to control said stimulation device and said recording device so as to effect a stimulation of at least one brain function during each of a plurality of measurement cycles, record at least one stimulation image of the brain operating field with said at least one stimulation brain function during the measurement cycle and record at least one reference image of the brain operating field without said at least one stimulated brain function during the measurement cycle;

said control and evaluation device being further configured to generate a map of the brain operating field using said at least one stimulation image recorded during the measurement cycle and said at least one reference image recorded during the measurement cycle;

said control and evaluation device being further configured to generate a signal for said display device and output said signal to said display device, wherein said signal is configured to cause said map to be displayed on said display device; and, said control and evaluation device being further configured to control said stimulation device and said recording device so as to cause a plurality of measurement cycles to be carried out;

said control and evaluation device being configured to generate a new map of the brain operating field after each one of the plurality of measurement cycles following a first measurement cycle, wherein, in order to generate said new map, said stimulation images and said reference images of one or more preceding measurement cycles are also used besides said at least one stimulation image recorded in the measurement cycle just carried out and said at least one reference image recorded in the measurement cycle just carried out;

said control and evaluation device being configured to update said signal for the display device after each measurement cycle in such a manner that at least said map generated after the measurement cycle just carried out is displayed on said display device; said control and evaluation device being further configured to examine the at least one stimulation image and the at least one reference image used for said generating the new map for disturbances and determine a numerical value representing a measure of the disturbances in the at least one stimulation image and the at least one reference image used for said generating the new map as a quality parameter;

said control and evaluation device being further configured to assign the quality parameter to the new map and display the quality parameter beside the new map; and, wherein the numerical value indicates a magnitude of a proportion of the brain tissue area affected by the disturbances in a total brain tissue area visible in the brain operating field.

21. The device of claim 20, wherein, after each measurement cycle following said first measurement cycle, said control and evaluation device updates said signal for said display device in such a way that in each case at least that map which was generated before said map generated after the measurement cycle just carried out is also displayed on said display device.

22. The device of claim 20, wherein said control and evaluation device is configured to control said stimulation device and said recording device in such a manner that a plurality of stimulation images and a plurality of reference images are recorded during the measurement cycle, and, said control and evaluation device uses the plurality of recorded stimulation images and reference images from each measurement cycle for generating said map of the brain operating field.

23. The device of claim 20, wherein said control and evaluation device enables a predefining of a maximum number ($N_{max}$) of measurement cycles and generates said signal for the display device in such a way that the number (N) of the measurement cycle after which the most up-to-date of the displayed maps was generated is also displayed in addition to the map or the maps on the display device.

24. The device of claim 23, wherein said control and evaluation device affords a possibility of terminating the generating of maps before reaching the maximum number ($N_{max}$) of measurement cycles.

25. The device of claim 20, wherein said control and evaluation device is further configured to examine said at least one stimulation image and said at least one reference image used for generating said map for disturbances; and, said control and evaluation device is further configured to generate the signal for said display device in such a manner that the disturbances that occurred in said at least one stimulation image and said at least one reference image on which the generated map is based are also displayed on the display device in addition to the generated map and/or said control and evaluation device is further configured to generate the signal for said display device in such a manner that a quality parameter assigned to said map is displayed on the display device in addition to said map, said quality parameter representing a measure of the disturbances that occurred in the stimulation images and reference images on which said map is based.

26. The device of claim 25, wherein the control and evaluation device is configured to generate the signal for said display device in such a manner that, after the end of all the measurement cycles, each map generated after the corresponding measurement cycle together with the disturbances that occurred in the at least one stimulation image and the at least one reference image on which the respective map is based, and/or together with the quality parameter assigned to the respective map, are displayed, wherein the control and evaluation device affords a user a possibility of sorting out individual measurement cycles; and, wherein the control and evaluation device newly generates a new map on the basis of the stimulation images and reference images of the measurement cycles that have not been sorted out.

27. The device of claim 20, wherein said control and evaluation device is configured to control said stimulation device and said recording device in such a manner that, before the first measurement cycle, indicators are determined for parameters which are relevant to the stimulation and to the recording of the stimulation images and the reference images, and said control and evaluation device is further configured to cause the indicators determined to be displayed on said display device.

28. A surgical microscope system comprising a surgical microscope and the device as claimed in claim 20.

* * * * *